(12) United States Patent
Strgar

(10) Patent No.: US 12,226,378 B2
(45) Date of Patent: *Feb. 18, 2025

(54) TOPICAL SUBSTANCE FOR VAGINAL USE

(71) Applicant: VAGINAL BIOME SCIENCE, INC., Eugene, OR (US)

(72) Inventor: Wendy Strgar, Eugene, OR (US)

(73) Assignee: VAGINAL BIOME SCIENCE, INC., Eugene, OR (US)

( * ) Notice: Subject to any disclaimer, the term of this patent is extended or adjusted under 35 U.S.C. 154(b) by 178 days.

This patent is subject to a terminal disclaimer.

(21) Appl. No.: 18/049,983

(22) Filed: Oct. 26, 2022

(65) Prior Publication Data

US 2023/0070915 A1  Mar. 9, 2023

Related U.S. Application Data

(63) Continuation of application No. 17/209,252, filed on Mar. 23, 2021, now Pat. No. 11,806,325, which is a continuation of application No. 16/191,292, filed on Nov. 14, 2018, now Pat. No. 10,952,979, which is a continuation-in-part of application No. 15/691,645, filed on Aug. 30, 2017, now Pat. No. 10,195,169, which is a continuation-in-part of application No. 15/294,340, filed on Oct. 14, 2016, now abandoned, which is a continuation of application No. 14/636,035, filed on Mar. 2, 2015, now Pat. No. 9,470,676.

(60) Provisional application No. 62/094,769, filed on Dec. 19, 2014.

(51) Int. Cl.
| | | |
|---|---|---|
| *A61K 31/191* | (2006.01) | |
| *A61K 9/00* | (2006.01) | |
| *A61K 9/06* | (2006.01) | |
| *A61K 47/02* | (2006.01) | |
| *A61K 47/12* | (2006.01) | |
| *A61K 47/36* | (2006.01) | |
| *A61K 47/38* | (2006.01) | |
| *G01N 33/50* | (2006.01) | |

(52) U.S. Cl.
CPC ............. *A61K 31/191* (2013.01); *A61K 9/00* (2013.01); *A61K 9/0034* (2013.01); *A61K 9/06* (2013.01); *A61K 47/02* (2013.01); *A61K 47/12* (2013.01); *A61K 47/36* (2013.01); *A61K 47/38* (2013.01); *G01N 33/50* (2013.01)

(58) Field of Classification Search
CPC .................................................. A61K 31/191
See application file for complete search history.

(56) References Cited

U.S. PATENT DOCUMENTS

| | | | |
|---|---|---|---|
| 5,466,463 A | 11/1995 | Ford | |
| 5,765,579 A | 6/1998 | Heiler et al. | |
| 5,778,886 A | 7/1998 | Shihata | |
| 6,045,786 A | 4/2000 | Cone et al. | |
| 6,892,732 B2 | 5/2005 | Wang et al. | |
| 8,367,098 B2 | 2/2013 | Maguire et al. | |
| 9,470,676 B2* | 10/2016 | Strgar | G01N 33/50 |
| 10,195,169 B2* | 2/2019 | Strgar | G01N 33/50 |
| 10,357,527 B2 | 7/2019 | Ellington et al. | |
| 10,952,979 B2* | 3/2021 | Strgar | A61K 47/02 |
| 11,806,325 B2* | 11/2023 | Strgar | A61K 9/06 |
| 2003/0039944 A1 | 2/2003 | Grueneberg et al. | |
| 2004/0132690 A1 | 7/2004 | Carmelia et al. | |
| 2009/0105314 A1 | 4/2009 | Ii et al. | |
| 2012/0195961 A1 | 8/2012 | Kritikou | |
| 2014/0147520 A1 | 5/2014 | Gupta et al. | |

FOREIGN PATENT DOCUMENTS

| | | |
|---|---|---|
| CN | 1113150 | 12/1995 |
| CN | 101559036 | 10/2009 |
| CN | 101773513 | 7/2010 |
| CN | 102512338 | 6/2012 |
| CN | 102266283 | 9/2012 |
| EP | 1582186 | 10/2005 |
| EP | 2018872 | 1/2009 |
| JP | 03264520 | 11/1991 |
| JP | 101430 | 1/1998 |
| KR | 20090054777 | 6/2009 |
| WO | 2001/095951 | 12/2001 |
| WO | 2006/075236 | 7/2006 |
| WO | 2014/152154 | 9/2014 |

OTHER PUBLICATIONS

Aroutcheva, et al., "Defense Factors of Vaginal Lactobacilli," Am. J. Obstet Gynecol, 2001, vol. 185(2), pp. 375-379.
Ayehunie, et al., "Hyperosmolal Vaginal Lubricants Markedly Reduce Epithelial Barrier Properties in a Three-Dimensional Vaginal Epithelium Model," Toxicology Reports, 2018, vol. 5, pp. 134-140.
Balance Activ Vaginal Gel (7x5ml Tubes) Product Information 2013, https:www.expresschemist.co.ukbalance_activ_vaginal_gel.html, pp. 2.
Berge, et al., "Pharmaceutical Salts," Journal of Pharmaceutical Sciences, 1977, vol. 66 (1), pp. 18.
Gynofit Gel with Lactic Acid, 2010, http://www.gynofit.com/milchsaeure-vaginalgel-en.html, pp. 2.
Gynofit Lactic Acid Vaginal Gel 5ml N6 Product Information 2013, http://ww.efarma.it, pp. 3.

(Continued)

*Primary Examiner* — Rei Tsang Shiao

(74) *Attorney, Agent, or Firm* — HSML P.C.

(57) ABSTRACT

Vaginal lubricants that have salts which are biomatched to salts that are naturally present in the vagina facilitate intercourse without toxic effects. Topical substances that have a low buffering capacity to promote fertility by providing lubricity while minimizing disturbance to the natural pH levels present during intercourse. A low buffering capacity reduces the extent to which a product interferes with natural pH and buffering capacity of fluids that are present during intercourse.

22 Claims, 5 Drawing Sheets

(56) References Cited

OTHER PUBLICATIONS

Manjakani Plus Feminine Wash with Kacip Fatimah, Product Information 2013 https://www.hervsforlove.com, pp. 2.
Moench, et al., "Microbicide Excipients Can Greatly Increase Susceptibility to Genital Herpes Transmission in the Mouse," BMC Infect. Dis., 2010, vol. 10 (331), pp. 9.
Natural Ecological Lubricant, Organic Products without Intermediaries, Product Information 2013, https://www.productosecologicossinintermediarios.es, pp. 3.
Owen, et al., "A Review of the Physical and Chemical Properties of Human semen and the Formulation of a Semen Simulant," J. Androl., 2005, vol. 26 (4), pp. 459-469.
Owen, et al., "A Vaginal Fluid Simulant," Contraception, 1999, vol. 59 (2), pp. 91-95.
Pre-Seed—Vaginal Lubricant, Product Information 2013, https://www.amazon.co.uk, pp. 6.
Rastogi, et al., Engineering and Characterization of Simplified Vaginal and Seminal Fluid Simulants, Contraception, 2016, vol. 93 (4), pp. 337-346.
Tien, et al., "In Vitro and in Vivo Characterization of a Potential Universal Placebo Designed for use in Vaginal Microbicide Clinical Trials," AIDS Res. Hum. Retroviruses, 2005, vol. 21 (10), pp. 845-853.
"Vegan Spermicide Alternative", Product Information 2013, https://vegan-love.com, pp. 7.
"Yes Intimate Lubricants", The Natural Skincare Company, Product Information 2013, https://www.thenaturalskincarecompany.co.k, pp. 4.

\* cited by examiner

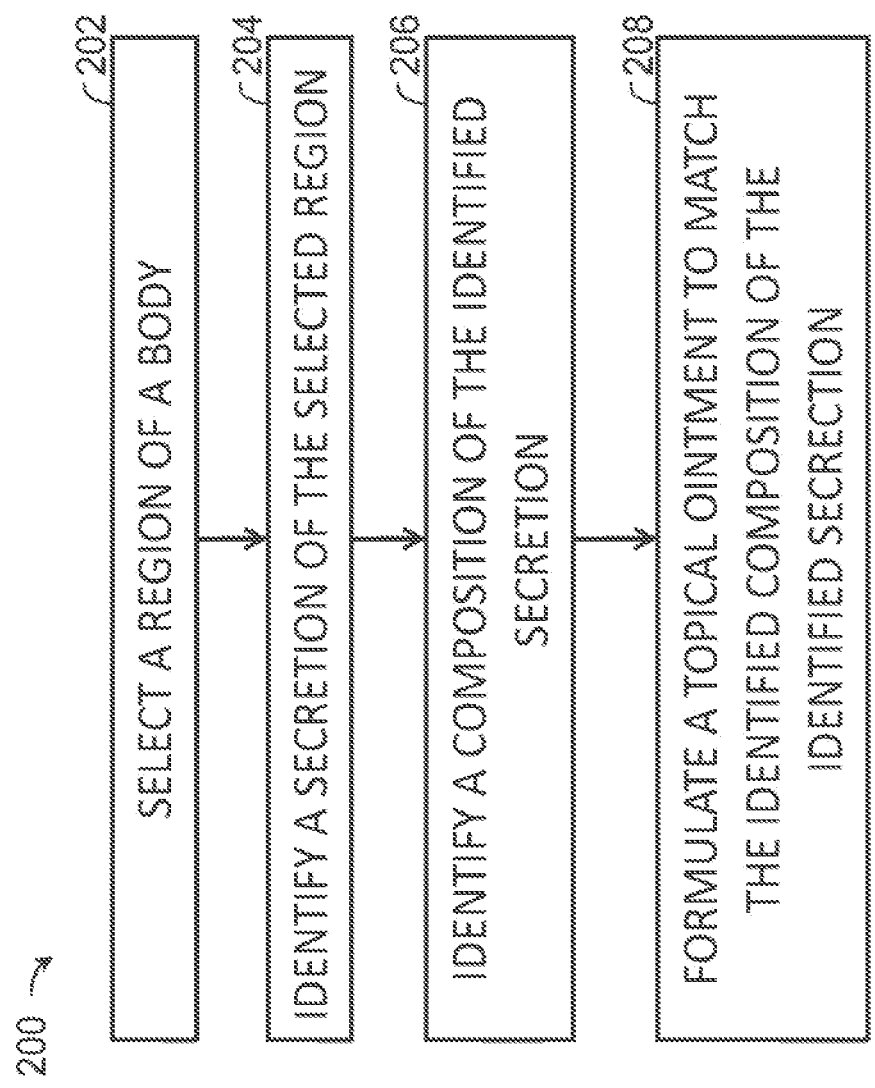

TOPICAL SUBSTANCE FOR VAGINAL USE

CROSS-REFERENCES TO RELATED APPLICATIONS

This application is a continuation of U.S. patent application Ser. No. 17/209,252, filed Mar. 23, 2021, which is a continuation of U.S. patent application Ser. No. 16/191,292, filed Nov. 14, 2018, which is a continuation in part of U.S. patent application Ser. No. 15/691,645, filed Aug. 30, 2017, which is a continuation in part of U.S. patent application Ser. No. 15/294,340, filed Oct. 14, 2016, now abandoned, which is a continuation of U.S. patent application Ser. No. 14/636,035, filed Mar. 2, 2015, which issued as U.S. Pat. No. 9,470,676, which application is based upon and claims the benefit under 35 U.S.C. § 119(e) of U.S. Provisional Patent Application Ser. No. 62/094,769, filed Dec. 19, 2014, which is incorporated herein by reference in its entirety for all purposes.

FIELD

This document relates to materials that are applied topically to the vagina to promote fertility.

INTRODUCTION

Portions of a human body typically secrete or produce various substances that may provide various benefits. For example, a mouth typically secretes saliva, which aids in digestion and provides lubrication for portions of the mouth. Microflora (e.g., including lactobacilli) of a vagina typically produce lactic acid, which may protect the vagina from various diseases, such as bacterial vaginosis (BV).

Often bodily secretions are supplemented with various over the counter (OTC) and/or prescription secretion supplements. For example, a person may supplement secretions produced by their lips with an OTC lip balm In another example, a female may supplement secretions produced by her vagina with an OTC or prescription personal lubricant.

However, pre-existing secretion supplements often include components that were presumed to be safe but that actually harm the portion of the body being supplemented. For example, pre-existing personal or vaginal lubricants, such as K-Y® jelly, often include components that may damage the vagina and/or may make the vagina more susceptible to disease. For example, pre-existing vaginal lubricants are often formulated to have pH values of 6-7, which are much higher than the acidic pH of the healthy vagina, which has a pH of around 3.5. This may allow sexually transmitted diseases (STDs) to occur and may lead to other diseases as well, such as BV.

Similarly, Pre-Seed®, a pre-existing pro-fertility lubricant, also does not have an acidic pH but rather has a somewhat alkaline pH of 7.29. This high pH alkalizes the vagina to promote the life of sperm, but by doing so may make the vagina more susceptible to HIV and other STD pathogens.

Further, pre-existing personal lubricants are formulated with an osmolality much greater than an osmolality of a typical vagina. Using such a personal lubricant may result in the cells of the vagina releasing fluid to dilute the personal lubricant, which may result in death of the cells, damage to the vagina, and/or subsequent dryness of the vagina.

Moreover, pre-existing vaginal products commonly include other various ingredients which are harmful to the vagina. For example, these vaginal products typically include detergents and surface-active agents, glycerol (glycerine) and other humectant/solvent excipients, and/or preservatives which typically include chlorhexidine and/or ethylenediaminetetraacetic acid (EDTA), among others. Detergents and surface-active ingredients are harmful because they are markedly toxic to mucosal epithelia, including that of the vagina. Such detergents and surface-active ingredients may include nonoxynol-9 and similar detergents, and glycerol monolaurate (GML). Glycerol (glycerine) and other humectant/solvent excipients are harmful because they increase vaginal susceptibility to disease. For example, Moench et al. (BMC Infectious Diseases 2010, 10:331) reported that the following excipients markedly increased susceptibility to HSV-2 after a single exposure: 5% glycerol monolaurate (GML) formulated in K-Y® Warming Jelly, 5% GML as a colloidal suspension in phosphate buffered saline, K-Y Warming Jelly alone, and both of its humectant/solvent ingredients (neat propylene glycol and neat polyethylene glycol (PEG-8)).

Conventional products that are marketed as being inserted into a vagina to promote fertility are typically formulated to match the pH of seminal fluids, which are alkaline, and buffered to preserve the alkalinity in the presence of an acid. Alkaline substances in a vagina can be harmful to a vagina, which is naturally acidic. Conventional fertility products often include toxic materials, or materials with a strong odor or flavor that may harm users and diminish sexual experience.

SUMMARY

Embodiments of the present application include a vaginal lubricant that comprises a solvent, a viscosity modifier, up to 0.5% by weight of a potassium salt, up to 1.5% by weight of a sodium salt, and up to 0.5% by weight of a calcium salt, and has an osmolality of from 100-500 mOsm/Kg. The lubricant may further comprise up to 0.5% by weight of a magnesium salt. The potassium salt may be potassium chloride (KCl), the sodium salt may be sodium chloride (NaCl), the calcium salt may be calcium chloride ($CaCl_2$)), and the magnesium salt may be magnesium chloride ($MgCl_2$).

In specific embodiments, the lubricant may have from 0.03% to 0.07% of the magnesium salt, from 0.15% to 0.35% of the potassium salt, from 0.07% to 0.12% of the calcium salt, and from 0.30% to 1.0% of the sodium salt. The lubricant may be isotonic with human vaginal fluid. In an embodiment, the lubricant has an osmolality from 300-400 mOsm/Kg. The lubricant may be non-toxic to the human vagina.

In one embodiment, the lubricant comprises from 0.15% to 0.35% of the potassium salt, from 0.01% to 0.12% of the calcium salt, and from 0.30% to 1.0% of the sodium salt. Embodiments of the lubricant may be a gel with a pH from 3.0-5.0. The lubricant may include up to 2% by weight of lactic acid.

A method of manufacturing a vaginal lubricant includes adding a viscosity modifier, a plurality of salts, and an acid to a solvent, wherein the plurality of salts comprises up to 0.5% by weight of a potassium salt, up to 1.5% by weight of a sodium salt, and up to 0.5% by weight of a calcium salt, so that the lubricant has a pH from 3.0 to 5.0, and an osmolality of from 100-500 mOsm/Kg. The method may further include adding up to 0.5% by weight of a magnesium salt. The solvent may be water. In an embodiment, the potassium salt is potassium chloride (KCl), the sodium salt is sodium chloride (NaCl), the calcium salt is calcium chloride ($CaCl_2$)), and the magnesium salt is magnesium chloride ($MgCl_2$). In addition, lactic acid may be added in an amount of from 0.2% to 2% by weight.

The potassium salt is added may be added in an amount of 0.15% to 0.35%, the sodium salt may be added in an amount from 0.15% to 0.35%, the calcium salt may be added in an amount from 0.01% to 0.12%, and the sodium salt may be added in an amount from 0.30% to 1.0%. The ingredients may be added to achieve an osmolality from 300-450 mOsm/Kg. The substance may be iso-osmolal with human vaginal fluid.

A topical substance that promotes fertility when applied to a human vagina may include a solvent, a plurality of salts dissolved in the solvent, and a viscosity modifier, and have a pH of from 3 to 5, and a buffering capacity such that adding 5 millimoles of NaOH to 1 gram of the substance increases the pH by at least 1. The substance may have an osmolality of 500 mOsm/Kg or less. In an embodiment, the substance is iso-osmolal with healthy human vaginal fluid.

In an embodiment, the plurality of salts includes up to 0.5% by weight of a potassium salt, up to 1.5% by weight of a sodium salt, and up to 0.5% by weight of a calcium salt. The salts may further include up to 0.5% by weight of magnesium salt. In an embodiment, the substance has from 0.03% to 0.07% of the magnesium salt, from 0.15% to 0.35% of the potassium salt, from 0.01% to 0.12% of the calcium salt and from 0.30% to 1.0% of the sodium salt. The substance may further comprise up to 0.02% by weight of sorbic acid, or from 0.001 to 0.01% by weight of sorbic acid.

An embodiment of the fertility promoting substance has up to 0.05% by weight of lactic acid. The only acidic ingredients of the substance may be the solvent and one or more of sorbic acid and lactic acid. The substance may be free from alkaline ingredients, and it may be non-toxic to the human vagina.

The substance may have a buffering capacity such that adding 2 millimoles of NaOH to 1 gram of the substance increases the pH by at least 1, or a buffering capacity such that adding 1 millimole of NaOH to 1 gram of the substance increases the pH by at least 1.

A method of forming a topical substance that promotes fertility when applied to a human vagina includes adding a plurality of salts and an acid to a solvent, and adding a viscosity modifier to the solvent to form a topical substance with a pH of from 3 to 5, and a buffering capacity such that adding 5 millimoles of NaOH to 1 gram of the substance increases the pH by at least 1. The plurality of salts may include up to 0.5% by weight of a potassium salt, up to 1.5% by weight of a sodium salt, and up to 0.5% by weight of a calcium salt. In addition, up to 0.5% by weight of magnesium salt may be added.

In an embodiment, the plurality of salts includes from 0.03% to 0.07% of a magnesium salt, from 0.15% to 0.35% of a potassium salt, from 0.01% to 0.12% of a calcium salt, and from 0.30% to 1.0% of a sodium salt. The substance may have an osmolality of 500 mOsm/Kg or less. In an embodiment, an amount of acids is added to the substance such that adding 1 millimole of NaOH to 1 gram of the substance increases the pH by at least 1.

The present invention provides systems and methods for bio-matching formulations (e.g., gels, creams, etc.) to a particular region (or part) of a living body, such as that of a human or other animal. Formulations and methods of formulating thereof may provide compositions that both supplement secretions of the particular region of the living body and promote the health of the particular region. In one embodiment, a method of bio-matching a topical gel is provided. The method may comprise selecting a vagina of a living female body; identifying a secretion of the selected vagina; identifying a composition of the identified secretion; and formulating the topical gel to match the identified composition of the identified secretion. The matching includes using a preselected type and quantity of lactic acid, and formulating to a preselected pH and salt composition.

In another embodiment, a topical gel for human use is provided. The gel may comprise a formulation matched to a composition of a particular part of a human body. The formulation may include lactic acid, and the particular part may be a vagina.

In another embodiment, a topical gel for human use may comprise a formulation including lactic acid having a racemic index in a range of about 50% L/50% D. The formulation may be matched to a composition (or chemistry thereof) of a particular part of a human body.

In another embodiment, a vaginal lubricant is provided. The lubricant may comprise a formulation including lactic acid having a racemic index that is bio-matched but not bio-identical to a racemic index of natural lubricants in a generally healthy vagina.

BRIEF DESCRIPTION OF THE DRAWINGS

FIG. 11 is a flowchart depicting a method of bio-matching a topical gel to a living body.

DETAILED DESCRIPTION

Figure 1:
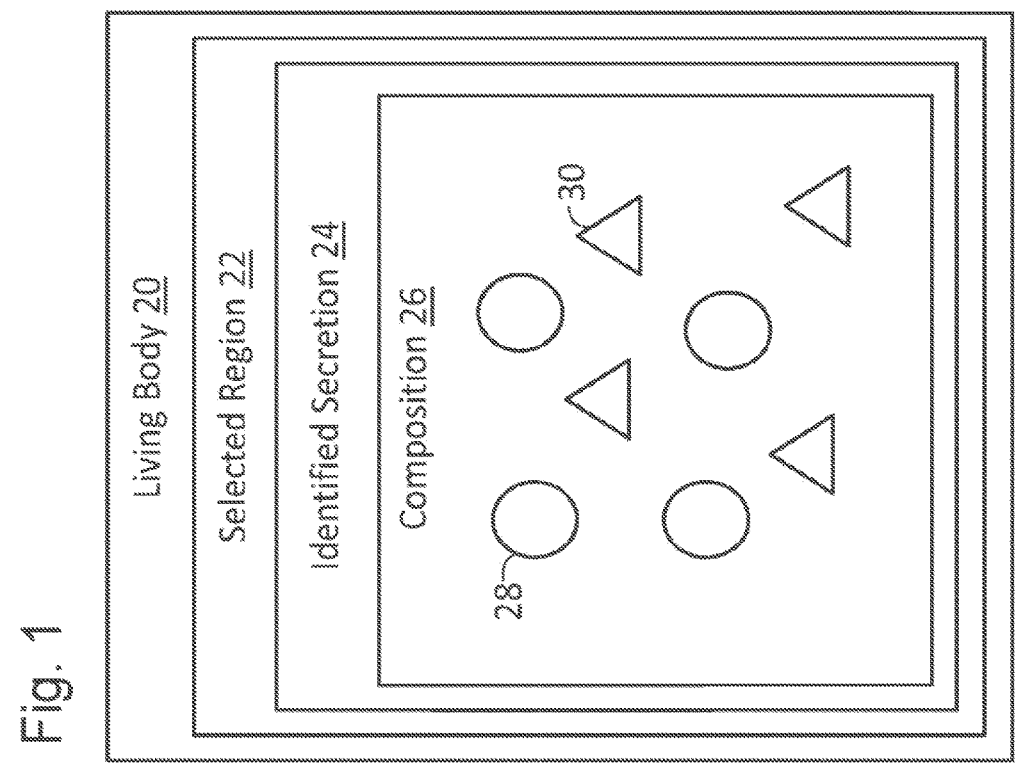
FIG. 1 is a block diagram schematically depicting a composition of an identified secretion of a selected region of a living body.

FIG. 1 shows a living body 20, which may be that of a human or other animal. In some embodiments, body 20 may be a body of a plant. Body 20 may have one or more regions (or components), such an eye region, an ear region, a vaginal region, a mouth region, and a rectal region among others. A selected region 22 of the one or more regions may produce one or more secretions for one or more purposes (e.g., to produce one or more desired effects). For example, a mouth region may produce saliva to lubricate the mouth region.

The one or more secretions of the selected region may include an identified secretion 24. For example, identified secretion 24 may be a secretion that has been identified as contributing substantially to producing the desired effect (e.g., mouth lubrication, digestion, tartar control, etc.) and/or to promoting the health of the region.

As shown in FIG. 1, identified secretion 24 may include composition 26, which may include one or more chemical compositions, ionic compositions, molecular structures, and/or molecular compositions. For example, the composition may include a first portion of a first type of composition 28, and a second portion of a second type of composition 30. FIG. 1 shows the first and second portions including equal amounts of compositions 28 and 30. In some embodiments, composition 26 may include more than two types of different compositions, and/or may include various ratios of portions thereof.

In some embodiments, body 20 may be a generally healthy body, region 22 may be a generally healthy region, and/or secretion 24 (and/or one or more components of composition 26) may be identified as contributing to the health of region 22 and/or body 20. For example, the composition of region 22 may correspond to a generally healthy composition (e.g., associated with microbiota of a generally healthy, or eubiotic vagina). For example, one or more components of composition 26 or characteristics or properties thereof may be associated with (or present in) generally healthy vagina secretions.

Figure 2:
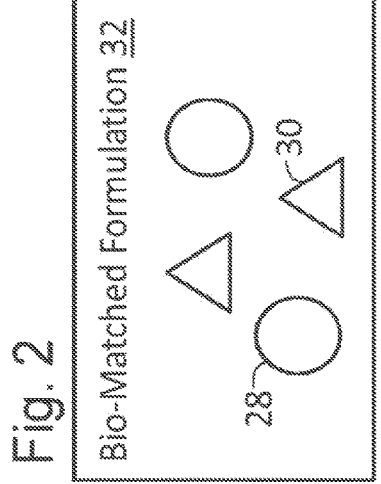
FIG. 2 is a block diagram schematically depicting a first formulation bio-matched to the composition of FIG. 1.

FIG. 2 shows a first formulation 32 that is bio-matched to body 20. For example, formulation 32 may be described as being bio-matched to composition 26. As shown, bio-matched formulation 32 includes a ratio of composition 28 to composition 30 that is equal to the ratio of composition 28 to composition 30 of secretion 24 in FIG. 1.

Figure 3:
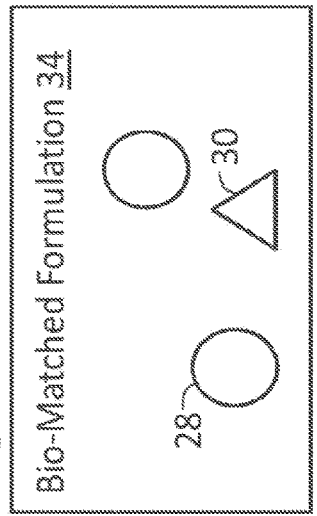
FIG. 3 is a block diagram schematically depicting a second formulation bio-matched but not bio-identical to the composition of FIG. 1.
Figure 4:
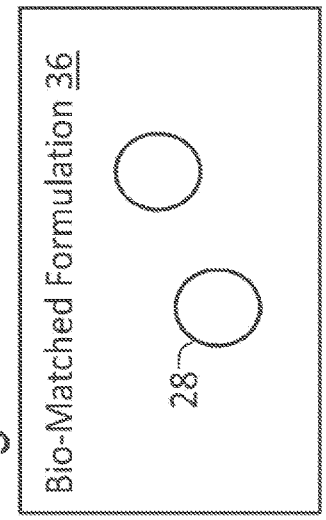
FIG. 4 is a block diagram schematically depicting a third formulation bio-matched but not bio-identical to the composition of FIG. 1.

In some embodiments, formulations bio-matched to secretion 24 may have ratios that are not equal to the ratio of compositions of secretion 24. For example, FIG. 3 shows a formulation 34 having a higher ratio of composition 28 to composition 30 than secretion 24, and FIG. 4 shows a formulation 36 including composition 28 but no composition 30. Formulations 34 and 36 may be described as being bio-matched but not bio-identical to a chemistry (or a composition) of secretion 24 (see FIG. 1).

Formulation 34 and/or formulation 36 may be useful for promoting the health of region 22 (see FIG. 1) and/or the desired effect of secretion 24. For example, composition 28 (or a characteristic of composition 28) may be identified as a significant contributor to the health of region 22 and/or to the desired effect of secretion 24. For example, a higher ratio of composition 28 to composition 30 may be identified as promoting the health of region 22, in which case formulation 34 and/or formulation 36 may be applied to region 22 (or to another body having a corresponding region deficient in composition 28) to increase a supply of composition 28 in that region.

Bio-matching a formulation to body 20 may involve "bio-balancing" the formulation to body 20. For example, ingredients (or compositions) that may be foreign to, produced by, or present in body 20 may be identified as possibly (or actually) detracting from (or harming) the health of region 22 (or body 20 as a whole). In this case, formulations 32, 34, and/or 36 may be bio-balanced by avoiding inclusion of one or more of these possibly or actually harmful ingredients (or compositions).

In some embodiments of bio-balancing a formulation to a vagina, harmful ingredients to avoid may include detergents and surface-active agents, glycerol (or glycerine) and other humectant/solvent excipients, one or more preservatives such as chlorhexidine and EDTA, salt in a concentration that makes the formulation not isotonic in the vagina, and/or acid in a concentration that does not match that of a healthy vagina.

Typically, portions (or regions) of male and female human bodies secrete various natural substances (or secretions). For example, a portion of a female human body or a male human body (e.g., a gland, organ, or flora associated with the portion or an organ) may secrete or produce one or more particular substances (e.g., lactic acid, saliva, etc.) for one or more particular functions (e.g., lubricating, moisturizing, cell protection, cell repair, protection from pathogens or foreign matter such as dust, etc.).

For example, the female body may include eyes secreting a first substance, a scalp secreting a second substance, ears secreting a third substance, nostrils secreting a fourth substance, a mouth secreting a fifth substance (e.g., saliva), lips of the mouth secreting a sixth substance, armpits secreting a seventh substance, nipples secreting an eighth substance (e.g., pheromones), an epidermis secreting a ninth substance, genitalia secreting a tenth substance (e.g., lactic acid produced by microflora living in the genitalia), a rectum secreting an eleventh substance, and feet secreting a twelfth substance.

The male body may include similar portions secreting (or producing) similar substances. However, due to differences between males and females (e.g., hormonal differences, genetic differences, among others) portions of the male body may differ from portions of the female body, and portions of the male body may secrete substances (e.g., pheromones) that are different than the substances secreted by the female body. For example, the male may include a penis and a scrotum secreting respective thirteenth and fourteenth substances, and a mouth of the male may secrete saliva having a composition that is different than a composition of saliva from the mouth of the female.

The genitalia (commonly referred to as a vagina) of the female human body may include labia majora, labia minora, a vagina, a cervix, a uterus, a urethra, a clitoris, a mons pubis, a symphysis pubis, and ovaries. Typically, the labia majora and the labia minor lead to the vagina, the cervix, and the uterus; and the urethra leads from the urinary bladder out of the female body through the labia minora and the labia majora.

A generally healthy vagina may include (or produce, or have present therein) various natural lubricants. For example, microflora (or bacteria) of the vagina (e.g., lactobacilli) may produce a first anti-microbial lubricant (e.g., lactic acid). Typically, microflora (e.g., vaginal bacteria) of a generally healthy vagina is dominated by *Lactobacillus crispatus*, which generally produce equal amounts of L-lactic acid and D-lactic acid. Further, a membrane of a vaginal wall of the vagina may produce a second lubricant (e.g., moisture), mucus glands of the cervix may secrete a third lubricant (e.g., different variations of mucus before and during ovulation), and glands, such as glandula vestibularis major located near an opening to the vagina, may secrete a fourth lubricant (e.g., a fluid such as mucus) when the female is sexually aroused.

In particular, mucus from the glands of the cervix and/or moisture from the vaginal wall membrane may provide lubrication within the vagina, and the fluid from the glandula vestibularis major may moisten the labial opening of the vagina, which may make contact with this area more comfortable for the female.

Typically, the female and/or a sexual partner of the female may apply an additional lubricant to components of the genitalia the female, such as the vagina and/or the labia majora and the labia minora, to increase lubrication of the vagina, which may enhance the sexual experience and/or prevent breakage of a condom For example, the male 70 may roll a condom onto his penis, such that an inside portion of the condom is in contact with the penis. The male may then apply a personal lubricant, such as over the counter K-Y® jelly, to an outside portion of the condom. The female and the male may then engage in sexual intercourse, with the over the counter lubricant providing additional lubrication between the outside portion of the condom and the vagina. However, as previously described, pre-existing lubricants often include components (such as detergents like Nonoxynol-9) that are not bio-balanced to a healthy vaginal environment, and application of such components may make the vaginal environment more prone to disease or damage.

Accordingly, the applicant has discovered that formulating a composition (e.g., topical gel, cream, lubricant, etc.) to match a composition (e.g., chemical composition, and/or characteristics thereof) of a secretion of a selected region of a human body (e.g., a healthy vagina) may provide or enhance a desired effect (e.g., lubrication) and promote health.

Figure 5:
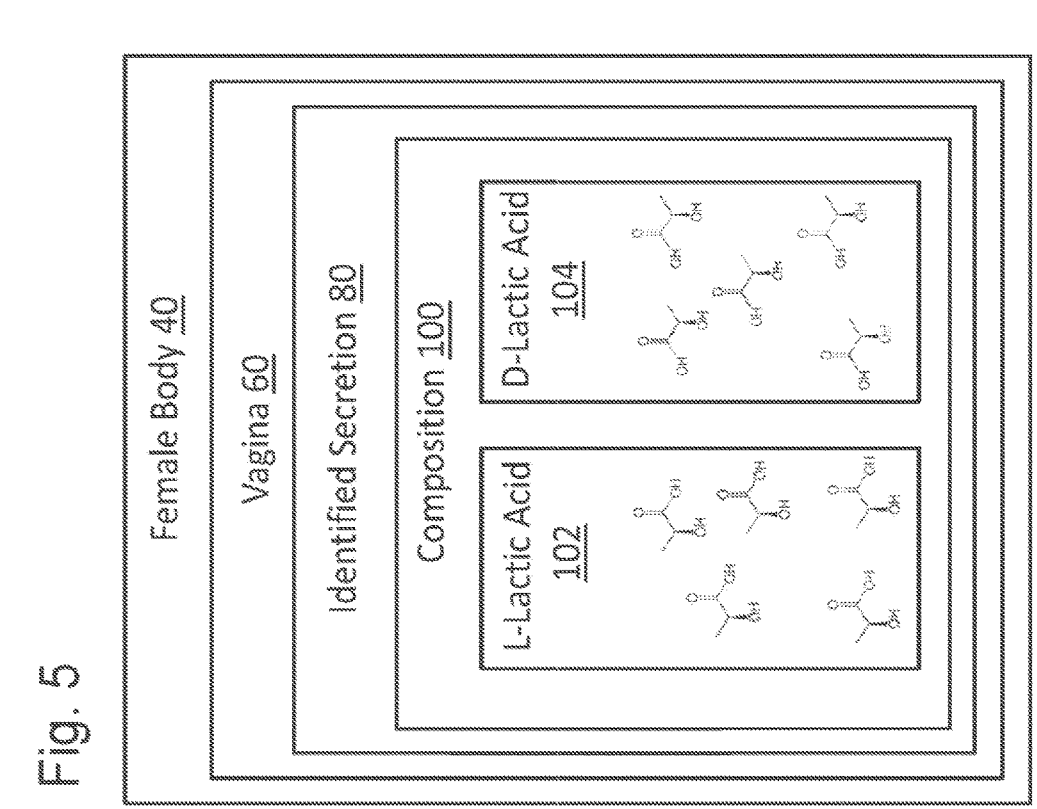
FIG. 5 is a block diagram of a female body, which schematically depicts a composition of an identified secretion of a vagina.

For example, FIG. 5 shows a schematic representation of a female body 40. A vagina 60 of body 40 may secrete one or more substances (or secretions), as previously described. The one or more substances may include an identified secretion 80 having a composition 100. If vagina 60 (and/or body 40) is relatively or generally healthy, then composition 100 may include L-lactic acid 102 (i.e., L-enantiomers) and D-lactic acid 104 (D-enantiomers), which are the two optical isomers of lactic acid. For example, microflora of a generally healthy vagina typically produces lactic acid comprising approximately 50% L-lactic acid and 50% D-lactic acid (i.e., lactic acid having a racemic index of about 50% L/50% D). In contrast, it has been found that BV more commonly occurs in vaginas with microflora that produce a large percentage of L-lactic acid and produce only a small percentage (or no percentage) of D-lactic acid.

To provide improved lubrication and vaginal health, applicant has formulated a vaginal lubricant that substantially matches an actual composition and/or characteristic of healthy vaginal secretions and that avoid inclusion of harmful ingredients (e.g., detergents, surface-active agents, glycerol, chlorhexidine, and EDTA). The result is a formulation that is bio-matched (or bio-balanced) to healthy vaginal secretions. Such a bio-matched vaginal lubricant should not include (or avoid inclusion of) any ingredient that might injure healthy vaginal lactobacilli. Rather, the bio-matched vaginal lubricant may include one or more of the following components and/or characteristics (or properties) that are substantially matched to the components and/or characteristics (or properties) of healthy vaginal secretions:

- an aqueous gel component—for example, the bio-matched vaginal lubricant may include a gel that does not include glycerol or other solvents, but only water (or comprises mainly water), as is true for mucus secretions of a healthy vagina;
- one or more viscoelastic properties—for example, the bio-matched vaginal lubricant may use a safe and natural polymer to create a gel with viscoelastic properties that match those of vaginal secretions (e.g., mucus) of a healthy vagina, which may include not only matching a viscosity of the vaginal secretions at a given shear rate, but also across a broad range of shear rates-more specifically, mucus of the vagina is a "shear-thinning" lubricant (e.g., a gel that becomes very slippery, and has a low viscosity when the gel is being sheared, as in the act of intercourse), and matching the viscoelastic properties of the vaginal lubricant to the mucus of the vagina may provide for the gel of the bio-matched vaginal lubricant not dripping out of the vagina, but remaining in the vagina and becoming very slippery with a low viscosity only when being sheared;
- an isotonic property—for example, the bio-matched vaginal lubricant may be formulated to have a salt composition that makes the bio-matched vaginal lubricant isotonic in the vagina (e.g., when the bio-matched vaginal lubricant is in the vagina, the bio-matched vaginal lubricant will not cause water to be secreted into the vagina, nor cause water to be absorbed out of the vagina);
- an isotonic property that matches as close as possible the salts present in a vaginal secretion (the salts in a vaginal secretion include sodium, potassium, calcium, and magnesium).
- a pH property—for example, the pH of the bio-matched vaginal lubricant may be formulated to closely match the pH of a healthy, or eubiotic vagina (e.g., pH 3.8±0.3%);
- a lactic acid component—for example, the bio-matched vaginal lubricant may be acidified with ~1±0.5% lactic acid, which is a concentration that may match that of a healthy vagina; and
- a racemic lactic acid component—for example, the bio-matched vaginal lubricant may include lactic acid that is an essentially racemic (equal) mix of the two optical isomers of lactic acid (i.e., the D- and L-isomers) to match the mixture of these isomers in a healthy vagina-more specifically, a healthy vagina is typically acidified by lactobacilli that produce both D- and L-isomers of lactic acid, but only a minority of women have these healthy, protective lactobacilli, and most other women either have few if any lactobacilli or have strains of lactobacilli that fail to make the D-isomer, and thus the bio-matched vaginal lubricant may be formulated to healthy vaginal secretions by including an approximately even mix of the two isomers (i.e., a racemic mix of D- and L-isomers of lactic acid).

With respect to achieving the desired biomatching property recited above, applicant has learned it is particularly important to biomatch iso-osmolality, pH, and 1% by weight racemic acid. The isotonic property recited above involves a salt composition that is isotonic with vaginal fluid. Isotonicity can be achieved with variations in sodium, and potassium chlorides as well as with other osmotically active compounds.

Osmolality of healthy vaginal secretions has been measured, and using that measurement, the invention includes a gel that biomatches osmolality to that of a healthy vagina. Based upon that biomatching, the invented lubricant, including a gel version, is as close to being isotonic as is possible. Biomatching, that is, matching the osmolality of vaginal secretions is the best way to achieve isotonicity, given the absence of any direct observations of fluid movement into or out of the vagina. The invented lubricant is isotonic, that is, for example, the gel version is effective to lubricate a human vagina that is neither: (i) hypertonic (causes the vaginal epithelium to secrete fluid that dilutes the lubricant which can cause toxicity in the vagina), nor (ii) hypotonic (causes fluid to be withdrawn from the vagina and drying it).

Further, the applicant has found that formulating a vaginal lubricant to match the vaginal acidity of a healthy vagina, particularly by including lactic acid in the formulation, and more specifically by including lactic acid that is substantially racemic, kills HIV and many other pathogens.

Recent studies have established harm caused to vaginal epithelial tissue [1]. Most of the widely used vaginal lubricants in the U.S. and Europe are strongly hyperosmolal, formulated with high concentrations of glycerol, propylene glycol, polyquaternary compounds or other ingredients that make these lubricants 4 to 30 times the osmolality of healthy vaginal fluid. Hyperosmolal formulations have been shown to cause marked toxicity to human colorectal epithelia in vivo, and significantly increase vaginal transmission of genital herpes infections in the mouse/HSV model. They also cause toxicity to explants of vaginal epithelia, to cultured vaginal epithelial cells, and increase susceptibility to HIV in target cells in cell cultures.

Hyperosmolal lubricants induce greater epithelial damage than hypo- and iso-osmolal lubricants. Given the level of breach in the epithelial barrier by hyperosmolal lubricants, there is potential of an increase in susceptibility to sexually transmitted infections such as HIV and HSV in individuals who are regular users of hyperosmolal lubricants. Such effects could be attributed to reduction in barrier integrity of the epithelium, which makes the epithelium "leaky" to allow viral and microbial entry, and alteration of the microbiota in the vaginal environment.

Hyperosmolal personal lubricants such as KY Jelly, and the surfactant N9 have been found to be toxic to lactobacilli that can help protect against infections by acidifying the vagina with lactic acid, a broad antiviral and anti-bacterial agent. While toxicity of hypo-osmolal agents is minimal, hyperosmolal concentrations of glycerol and propylene glycol cause obvious toxicity that increases markedly as the osmolality increases.

Lubricants containing glycerin/glycol, propylene glycol, and Polyethylene glycol (PEG-8) as one of the top four ingredients are associated with marked reduction in barrier properties and tissue morphological damage. The presence of glycerin as an ingredient may also contribute to an increase in osmolality which results in the loss of the apical layer in RepHresh exposed Epivaginal tissues. The reduction in barrier function has been shown quantitatively by a reduction in trans-epithelial electrical resistance (TEER).

Historically, the significance of a highly toxic agent, the detergent nonoxynol-9 (N9), was not adequately realized until after performing large HIV prevention trials of N9. N9 was, and still is, used as a vaginal contraceptive. Despite its significant toxic effects, it does not cause obvious pain or discomfort in most users.

Similarly, hyperosmolal lubricants cause little or no obvious pain or discomfort to most users. However, they have been shown to be toxic nonetheless, and to increase susceptibility to STDs. Sexual lubricants have been associated in several studies with increased risk of episodes of bacterial vaginosis, and most sexual lubricants are hyperosmolal with respect to the osmolality of healthy vaginal fluids. Hyperosmolal vaginal lubricants disrupt barrier functions of the basal and parabasal layers and shedding of the apical layers, which suggest osmolality induced disruption of epithelial barrier may be one of the mechanisms by which use of vaginal lubricants is associated with the risk of bacterial vaginosis and may increase susceptibility to sexually transmitted infections.

Figure 6:
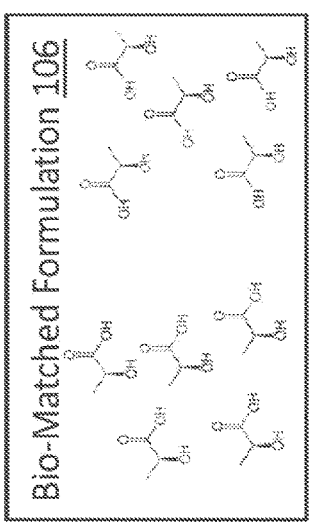
FIG. 6 is a block diagram schematically depicting a first formulation bio-matched to the composition of FIG. 5.

FIG. 6 shows a first formulation 106 that is bio-matched to a chemistry of body 40 of FIG. 5 (e.g., to a chemistry of secretion 80 of vagina 60). For example, FIG. 6 shows formulation 106 including 50% L/50% D racemic lactic acid. In some embodiments, formulation 106 may include lactic acid having a racemic index of about 10% L/90% D. In some embodiments, formulation 106 may include lactic acid having a racemic index of about 20% L/80% D. In some embodiments, formulation 106 may include lactic acid having a racemic index of about 30% L/70% D. In some embodiments, formulation 106 may include lactic acid having a racemic index of about 40% L/60% D. In some embodiments, formulation 106 may include lactic acid having a racemic index of about 60% L/40% D. In some embodiments, formulation 106 may include lactic acid having a racemic index of about 70% L/30% D. In some embodiments, formulation 106 may include lactic acid having a racemic index of about 80% L/20% D. In some embodiments, formulation 106 may include lactic acid having a racemic index of about 90% L/10% D. In some embodiments, formulation 106 may include D-lactic acid, and no L-lactic acid.

In some embodiments, the racemic lactic acid (or lactic acid having another suitable racemic index) may comprise about 1% of formulation 106. For example, the racemic lactic acid may comprise about 0.5% to about 1.5% of formulation 106. In other embodiments, the racemic lactic acid (or lactic acid having another suitable racemic index) may comprise other suitable percentages of formulation 106. In some embodiments, the racemic lactic acid may be synthetically-derived. In other embodiments, the racemic lactic acid may be naturally-derived. Applying formulation 106 to vagina 60 may lubricate vagina 60, and may promote the health of vagina 60.

Figure 7:
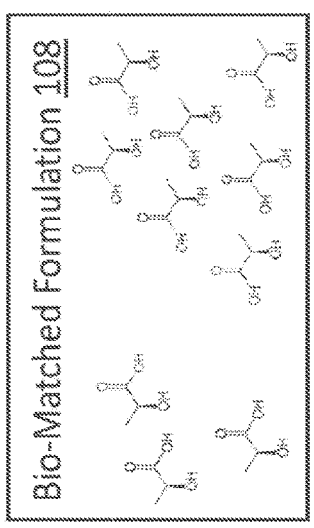
FIG. 7 is a block diagram schematically depicting a second formulation bio-matched but not bio-identical to the composition of FIG. 5.
Figure 8:
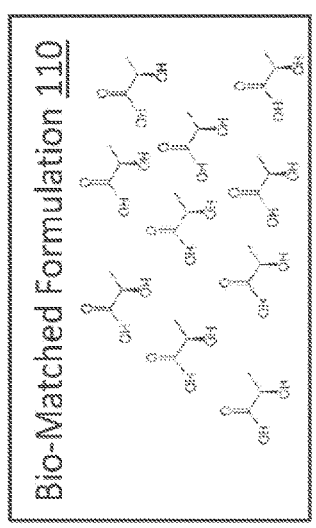
FIG. 8 is a block diagram schematically depicting a third formulation bio-matched but not bio-identical to the composition of FIG. 5.

FIGS. 7 and 8 show respective formulations 108 and 110, which may be considered as bio-matched to composition 100 of secretion 80 of FIG. 5. For example, FIG. 7 shows formulation 108 including lactic acid having a racemic index of 30% L/70% D, which may be suitable for application to a vagina that is slightly deficient in D-lactic acid. FIG. 8 shows formulation 110 including D-lactic acid, but no L-lactic acid, which may be suitable for application to a vagina that has a greater deficiency of D-lactic acid (or does not produce any D-lactic acid at all).

Figure 9:
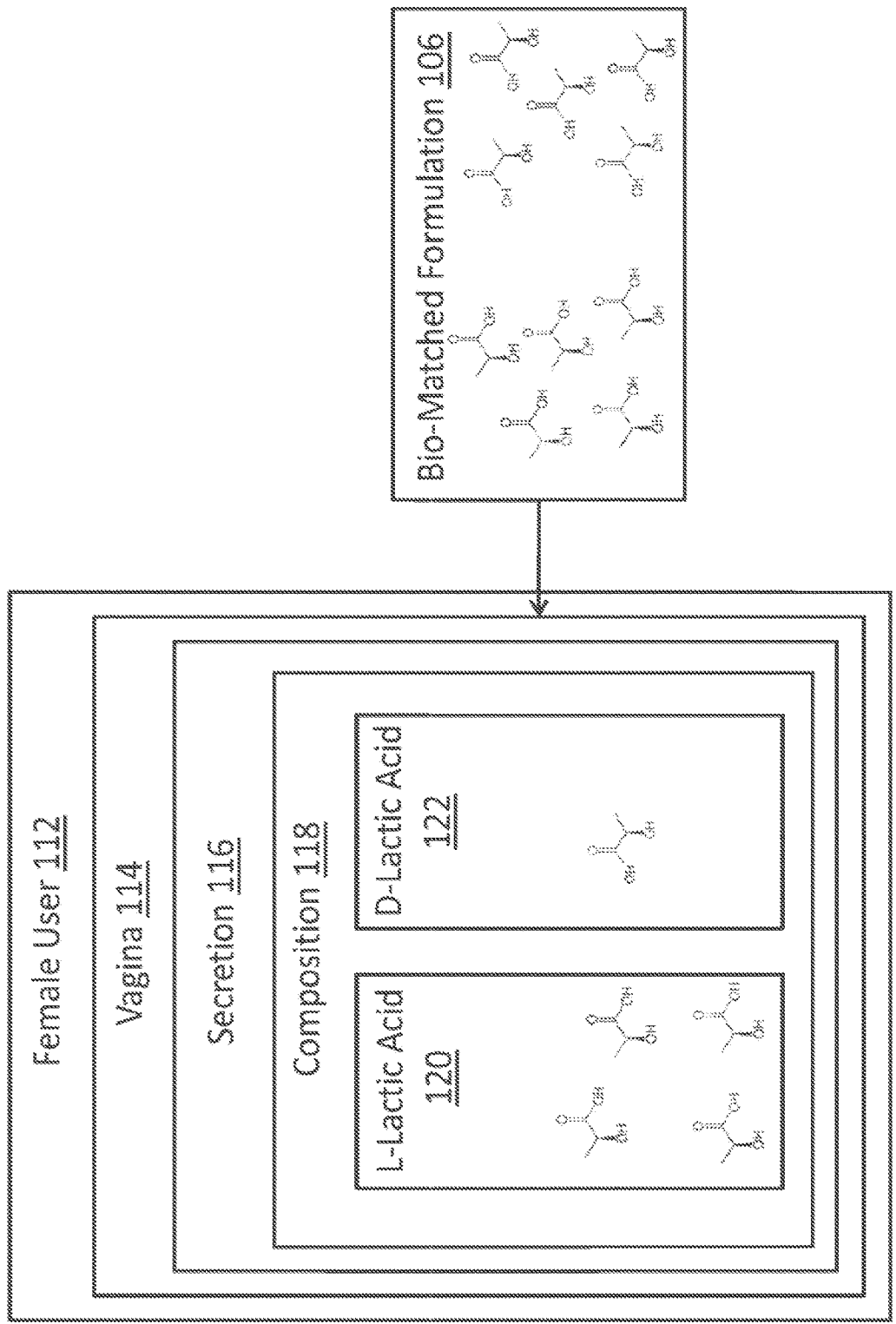
FIG. 9 is a block diagram schematically depicting the bio-matched formulation of FIG. 6 being applied to an unhealthy vagina of a female user.

FIG. 9 shows a schematic representation of a female user 112 having a vagina 114 that produces a secretion 116. Secretion 116 may include a composition 118, which may comprise lactic acid including L-lactic acid 120 and D-lactic acid 122. As shown, the lactic acid of secretion 116 has a racemic index of 80% L/20% D, which may be associated with a generally unhealthy condition of vagina 114 (or a condition prone to disease). Application of formulation 106 to vagina 114 may both lubricate vagina 114 and promote the health of vagina 114 (and female user 112). For example, formulation 106 may be added to secretion 116 to produce a supplemented secretion 124 (see FIG. 10).

Figure 10:
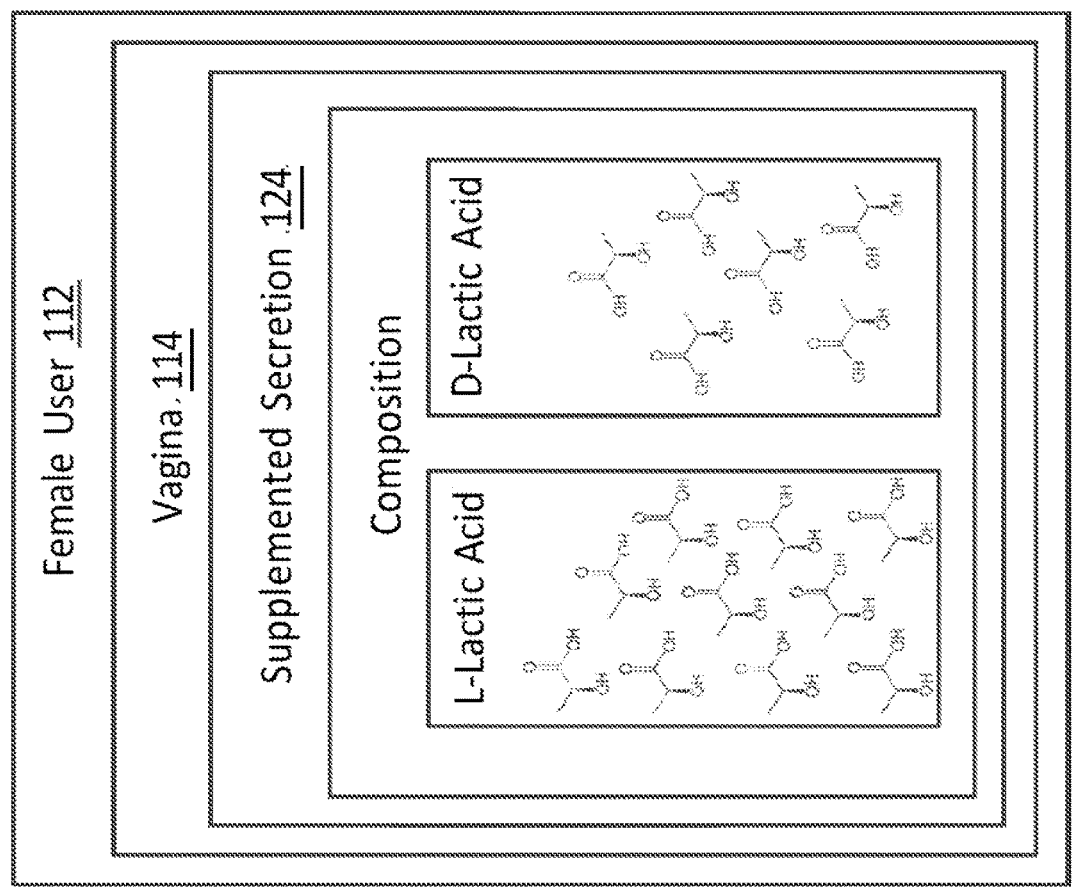
FIG. 10 is a block diagram of the female user of FIG. 9 after application of the bio-matched formulation.

FIG. 10 shows a schematic representation of female user 112 after application of formulation 106 (see FIG. 9) to vagina 114. As shown, supplemented secretion 124 of vagina 114 includes lactic acid having a racemic index of about 62.5% L/37.5% D, which may more closely match the lactic acid produced by microflora of a healthy vagina.

FIG. 11 shows an exemplary method, generally indicated at 200, of bio-matching a topical gel (or cream, lubricant, or other suitable substance) to a living body.

Method 200 may include a step 202 of selecting a region of the body. Step 202 may involve selecting a region including one or more components, such one or more glands, one or more organs, and/or flora (e.g., microflora including bacteria) that secrete various substances. For example, these components may secrete one or more particular substances (e.g., lactic acid, saliva, etc.) for one or more particular functions (e.g., lubricating, moisturizing, cell protection, cell repair, excretion of waste, protection from pathogens or foreign matter such as dust, etc.). The selected body may be a human body, and the selected region may be a vagina.

Method 200 may include a step 204 of identifying a secretion of the selected region. Step 204 may involve selecting a secretion produced by (or present in) a generally healthy region, such as a generally healthy vagina.

Step 204 may involve identifying a secretion that a relatively healthy body (or part thereof) produces. For example, microflora of a generally healthy vagina typically produces lactic acid comprising approximately 50% L-lactic acid (i.e., L-enantiomers) and 50% D-lactic acid (i.e., D-enantiomers). In contrast, as previously described, BV more commonly occurs in vaginas with microflora that produce lactic acid with little or no percentage of D-lactic acid. Accordingly, step 204 may involve identifying lactic acid having L-enantiomers and D-enantiomers.

Method 200 may include a step 206 of identifying a composition (e.g., chemical composition, molecular composition, ionic composition, or characteristics or properties thereof) of the identified secretion. Step 206 may involve identifying lactic acid. Step 206 may involve identifying lactic acid having a racemic index in a range of about 50% L/50% D.

Method 200 may include a step 208 of formulating the topical gel to (substantially) match the identified composition of the identified secretion. Step 208 may involve selecting lactic acid that is approximately racemic. Step 208 may involve selecting synthetic acid. Step 208 may involve selecting racemic synthetic acid. Step 208 may involve selecting pure racemic synthetic acid having a racemic index of 50% L/50% D. Step 208 may involve formulating the topical gel to include about 1% lactic acid (synthetic and/or racemic). In some embodiments, step 208 may involve bio-balancing the topical gel to avoid (or by avoiding) inclusion of one or more ingredients that are toxic (or harmful) to microbiota of the generally healthy vagina (or any vagina). Examples of ingredients that are toxic (or harmful) to the microbiota of a vagina include detergents, surface-active agents, glycerol, many types of preservatives including chloride and EDTA, salt concentrations/formulations that make the formulation non-isotonic in the vagina, and acid/base concentrations/formulations that do not match the pH of the generally healthy vagina.

Method 200 may further comprise applying the topical gel to the selected region of the human body (or a region of another human body corresponding to the selected region). For example, method 200 may further comprise applying the topical gel to a vagina. For example, applying the topical gel may involve rolling a condom onto a penis, such that an inner surface of the condom contacts the penis; disposing the topical gel onto an outer surface of the condom; and bringing the vagina into contact with the outer surface of the condom.

In some embodiments, the topical gel may be disposed on the condom prior to the condom being rolled onto the penis. For example, the topical gel may be disposed on the condom (e.g., the outer and/or inner surface) during a manufacturing and/or packaging step of the condom.

In other embodiments, the topical gel may be provided in a package or tube that is separate from a package containing a condom. For example, the topical gel may be provided in a stand-alone container. The user may open the container and apply the topical gel directly to the vagina, directly to the penis, and/or to any suitable surface of a condom.

In some embodiments, method 200 may further comprise applying the topical gel to a suitable medical device. For example, the topical gel may be suitable for lubricating one or more implements used during a pelvic exam, such as an outer surface of a glove disposed on a hand of a gynecologist.

EXAMPLE 1

The following is to prepare a vaginal lubricant according to a first version of the invention, with percentages by weight of the total formulation shown parenthetically after each component. Certified organic aloe vera powder (95%), commercially available under the trademark SD 200x™, is hydrated in a separate mixing tank. Agar (0.2%) is added to hydrated aloe vera powder, and the mixture is pasteurized by heating it to 160 degrees F. for about thirty (30) minutes. After allowing the mixture to cool to about 115 degrees F., Xanthan gum (3.1%) is added. The following inorganic ingredients are combined in a separate mixing container potassium sorbate (0.25%), sodium benzonate (0.20%) and natural flavor (0.35%). After being suitably mixed, the inorganic ingredients are added to the aloe vera mixture. Lactic acid (0.9%) is suitably mixed into the aloe vera mixture to match to the desired pH of vaginal secretions. The resulting mixture is tested at completion and prior to dispensing into commercial containers for microbial count. Microbial count is tested by using commercially recognized bacterial challenge tests, to meet the standard of no more than ten colony forming units (CPUs) present. Other quality control tests are performed, including commercially known 30-day shelf/oven testing, and freeze/thaw testing.

EXAMPLE 2

The following is to prepare a vaginal lubricant according to a second version of the invention, with percentages by weight of the total formulation shown parenthetically after each component. Certified organic aloe vera powder (95%), commercially available under the trademark SD 200x™, is hydrated in a separate mixing tank. Agar (0.2%) is added to hydrated aloe vera powder, and the mixture is pasteurized by heating it to 160 degrees F. for about thirty (30) minutes. After allowing the mixture to cool to about 115 degrees F. Xanthan gum (3%) is added. The following inorganic ingredients are combined in a separate mixing container potassium sorbate (0.25%), sodium benzonate (0.20%) and natural flavor (0.35%). After being suitably mixed, the inorganic ingredients are added to the aloe vera mixture. Racemic lactic acid (1%) is suitably mixed into the aloe vera mixture to bring the pH of that mixture within the range of 3.5-3.9. Microbial count is tested by using commercially recognized bacterial challenge tests, to meet the standard of no more than ten colony forming units (CPUs) present. Other quality control tests are performed, including commercially known 30-day shelf/oven testing, and freeze/thaw testing.

EXAMPLE 3

The following is to prepare a vaginal lubricant according to a third version of the invention, following a procedure as described in connection with Examples 1 and 2, and with percentages by weight of the total formulation shown parenthetically after each component.

| Component | Percentage by weight | Function |
| --- | --- | --- |
| Water | 94.5-97.5% | Solvent |
| Hydroxy ethylcellulose | 0.5-1.5% | Viscosity modifier |
| Carrageenan | 0.25-0.90% | Binder |
| Ceratonia Siliqua (Carob) Gum | 0.07-0.30% | Binder |
| Xanthan Gum | 0.07-0.30% | Binder |
| Sodium Chloride | 0.25-0.70% | Osmolality modifier |
| Lactic Acid | 0.5-1.5% | pH adjuster |
| Sodium Hydroxide | 0.07-0.30% | pH adjuster |
| Potassium Sorbate | 0.15-0.4% | Preservative |
| Sodium Benzoate | 0.15-0.4% | Preservative |
| Calcium Chloride | 0.005-0.02% | Viscosity modifier |

According to recently published test results, healthy vaginal secretions have an osmolality of 370+/−10 mOsm/Kg, which is higher than the osmolality of most other bodily fluids, which is about 290+/−10 mOsm/Kg. The osmolality of this above-identified version of the invention is 350+/−10 mOsm/Kg.

The primary gelling agent in the third version is HEC (hydroxyethylcellulose), and the secondary gelling agent is Carrageenan, a nontoxic material made from seaweed. Utilizing Carrageenan causes the third version to have the added feature of tending to minimize HSV and HPV infections. The primary salt ions used in the third version are Na, K, Cl, and Ca, and that same combination is found in the vagina. While the concentrations of those four salts are not identical to those in a healthy vagina, the combination of those four salts have been adjusted such that this third version has an osmolality that matches the osmolality of healthy vaginal secretions.

Biomatching salt content to healthy vaginal fluid has numerous benefits. In addition to providing a healthy osmolality, biomatching salt content minimizes disruption of natural conditions to which bacterial flora are adapted. Introducing a substance that alters natural conditions can be harmful to *Lactobacillus* and other vaginal flora. Accordingly, biomatched salt content promotes general health. Vaginal fluids are fluids that are present in a normal healthy vagina, and may comprise secretions from the endocervix and the vaginal epithelium.

Measured data suggests that healthy vaginal fluids have significant quantities of potassium salt, sodium salt, calcium salt, and magnesium salt. Embodiments of a biomatched lubricant may include potassium salt as potassium chloride (KCl), sodium salt as sodium chloride (NaCl), calcium salt as calcium chloride ($CaCl_2$)), and magnesium salt as magnesium chloride ($MgCl_2$). Embodiments may include up to 0.5% by weight of a potassium salt, up to 1.5% by weight of a sodium salt, up to 0.5% by weight of a calcium salt, and up to 0.5% by weight of magnesium salt. In some embodiments, the salts may be included in a range of from 0.03% to 0.07% of the magnesium salt, from 0.15% to 0.35% of the potassium salt, from 0.005% to 0.12% of the calcium salt, and from 0.30% to 1.0% of the sodium salt.

Low Buffering Capacity for Promoting Fertility

Embodiments of the present disclosure are directed to a product that safely lubricates the vagina while promoting fertility. Many conventional vaginal lubricants have a pH that is roughly matched to the pH of the human vagina, which is acidic. However, semen is alkaline with a pH that is typically in the range of about pH 7.1-8.0. An acidic vaginal lubricant can lower the pH of semen, which can be toxic to sperm Accordingly, conventional vaginal lubricants inhibit fertility by harming sperm.

Therefore, conventional fertility products typically have a pH that is formulated to promote sperm health. pH values of conventional fertility products are typically in the range from about 7 to 8. In addition, conventional fertility products are typically buffered to maintain a stable pH in the 7-8 range. The buffering capacity of conventional fertility products causes them to neutralize the acidic environment of the vagina, which can cause harm to a user, including destruction of natural flora and damage to vaginal cells.

Fertility promoting products are often used by couples that are having difficulty conceiving. There are many physiological inhibitions to fertility that prevent or inhibit fertility regardless of the pH levels during intercourse. As a result, couples may use fertility products frequently for an extended period of time, which can cause significant damage when the products are buffered to protect sperm. The additional damage to the vagina may make it even more difficult to conceive. Accordingly, conventional fertility products may end up harming users and ultimately making it more difficult to conceive than it would be if those products were never used.

Embodiments of the present disclosure overcome the shortcomings of conventional fertility products. In an embodiment, a product that is applied to the vagina has a low buffering capacity. A product with low buffering capacity has minimal effect on the pH levels of fluids in which it is in contact, thereby minimizing the impact that the product has on the natural pH levels that are present during intercourse.

In one embodiment, a product with minimal buffering capacity is formulated to have a pH within the range of a normal human vagina. Although there is no definitive consensus on a value or range of the acidity of a healthy vagina, it is generally recognized to be within the range of 3.1 to 4.5, and a majority of healthy vaginas have a pH of 3.5-4.1. Accordingly, a product that promotes fertility in the vagina may have an initial pH from 3.0-6.0, 3.1-4.5, or 3.5-4.1.

A useful designation concerning the buffering capacity of a buffer solution is the designation of the buffer's Van Slyke buffer value p. The Van Slyke buffer value β indicates the resistance of the buffer to change in pH upon addition of a strong acid or base, and is defined by the ratio $\Delta B/\Delta pH$, where B is the increment of completely dissociated base or acid in gram-equivalents per liter required to produce a unit change in pH (Van Slyke, Biol. Chem 52, 525-570, 1922). Thus, Slykes are the units of buffer strength (β) derived from the formula $\beta=B/1$ pH, where B is millimoles (mM) of 1N strong acid or base.

The buffering capacity of semen has been measured at 35.6±12.3 slykes, where $\beta_{7-6}=35.6\pm12.3$ mM, and the buffering capacity of vaginal fluid has been measured at 37.5±5 slykes, which may be expressed as $\beta_{4.2-5.2}=37.5\pm5$ mM. [2]

A vaginal product that promotes fertility may have a buffering capacity that is less than the buffering capacities of semen and vaginal fluids. In some embodiments, the buffering capacity of a vaginal product that promotes fertility is 50% or less, 25% or less, or 10% or less than a value within the range of the buffering capacity of semen or vaginal fluid. More specifically, an embodiment of the present disclosure may have a buffering capacity of 20 slykes or less, 10 slykes or less, 5 slykes or less, 2 slykes or less, or less than 1.0 slykes.

There are advantages and disadvantages to formulations within these ranges. When buffering capacity is higher, a fertility enhancement product can help preserve a natural pH from being altered by other substances that may be present during intercourse, such as other fertility promoting products or materials that are otherwise meant to enhance pleasure during intercourse. On the other hand, when buffering capacity is lower, a formulation will minimize disruption to the natural pH of vaginal secretions and sperm. A low buffering capacity can be achieved by minimizing the concentration of ingredients in a product that buffer pH levels.

The following table provides an example of a set of ingredients that are present in an embodiment of a vaginal lubricant that promotes fertility. Embodiments of the present disclosure are not limited to the specific values and ingredients in the table.

EXAMPLE 4

| Component | Percentage by weight | Function |
| --- | --- | --- |
| Water | 90-99% | Solvent |
| Hydroxy ethylcellulose | 0.5-5.0% | Viscosity modifier |
| Sodium Chloride | 0.1-1.5% | Biomatched Salt |
| Potassium Chloride | 0.001-1.5% | Biomatched Salt |
| Calcium Chloride | 0.001-1.5% | Biomatched Salt |
| Magnesium Chloride | 0.001-1.5% | Biomatched Salt |
| Lactic Acid | 0-0.03% | Weak acidic buffer |
| Potassium Sorbate | 0.001-0.1% | Preservative & weak buffer |
| Sorbic Acid | 0.001-0.1% | Preservative |

The primary constituent of the product described by Example 4 is water which acts as a solvent. The water may be deionized water or water that has otherwise been purified to remove materials that could react with other ingredients or biological fluids. Hydroxyethylcellulose is present as a viscosity modifier that creates a gel and provides lubricity. The listed functions of the ingredients are merely illustrative, and other purposes are possible.

Persons of skill in the art will recognize that it is possible to provide additional ingredients, and to substitute known ingredients for the specific ingredients listed in Example 4 in other embodiments. Some of the key properties of Example 4 include an osmolality that is biomatched to the osmolality of a vagina, salt content and pH that are biomatched to vaginal secretions, and a buffer capacity that is significantly lower than the buffer capacity of seminal fluids. The formula of Example 4 does not include any materials that are toxic or otherwise harmful to the vagina in the listed concentrations—on the contrary, most of the ingredients are naturally present in the human vagina.

The hydroxyethlycellulose is included as a viscosity modifier, or gelling agent. A gel provides lubricity as well as cohesion between molecules in a lubricant, which helps the lubricant to remain in the vagina during intercourse. When large amounts of viscosity modifier are present, formulations become tacky and lose lubricity. Persons of skill in the art will recognize that it is possible to use one or more viscosity modifiers other than hydroxyethylcellulose to create a non-toxic biocompatible gel. Accordingly, embodiments are not limited to the specific viscosity modifiers provided in the Examples.

Some embodiments have concentrations of ingredients that vary from the concentrations provided in the table above. Sodium chloride may be provided in concentrations from 0.5-1.0% or 0.65-0.85%, potassium chloride may be provided in concentrations from 0.1-0.5% or 0.2-0.3%, calcium chloride may be provided in concentrations from 0.01-0.20% or 0.06-0.12%, magnesium chloride may be provided in concentrations from 0.01-0.15% or 0.03-0.07%, sorbic acid may be provided in concentrations from 0.001- 0.01% or 0.002-0.008%, and lactic acid may be provided in concentrations from 0.00-0.05% or 0.00-0.15%. For a product that promotes fertility, lactic acid may be present in a lower concentration than a product for general lubrication and vaginal health to minimize the buffering capacity of the pro-fertility product.

In a lubricant that promotes fertility, salt content may be selected to biomatch one or both of seminal plasma and vaginal fluids. In particular, magnesium is present in seminal plasma at levels that are not found in vaginal fluids, so a magnesium salt that is not added to a lubricant that is biomatched to vaginal fluids may be included in a pro-fertility product. In a preferred embodiment, a lubricant that promotes fertility is formed by adding salts to approximately match a combination of seminal and vaginal fluids.

EXAMPLE 5

Batches of vaginal lubricant were prepared by combining the salts, sorbic acid, lactic acid and potassium sorbate with water and stirring vigorously. Hydroxyethylcellulose was sifted in while continuing to stir the solution to create a gel. It was determined that lubricant prepared with the ingredients and ranges described in Example 4 can be combined to create lubricants with a pH within the range of 3.1-4.5, an osmolality of up to 500 mOsm/kg, and a buffer capacity of from about 1-10 slykes. The osmolality values can be adjusted by varying the amount of salts, and the pH and buffering capacity can be adjusted by varying the amount of acid. Lubricants with such low buffering capacities will not significantly alter the pH of the vagina, nor reduce the alkalinizing, sperm-supporting, action of semen. Its ionic composition will also support the viability of sperm.

The following paragraphs may provide further information regarding embodiments of the present disclosure.

A. A method of bio-matching a topical gel, the method comprising: selecting a region of a living body, wherein selecting the region involves selecting a vagina; identifying a secretion of the selected vagina; identifying a composition of the identified secretion; and formulating the topical gel to match the identified composition of the identified secretion.

A1. The method of paragraph A, wherein the body is a human body.

A2. The method of paragraph A, wherein identifying the secretion involves identifying a secretion present in a generally healthy vagina.

A3. The method of paragraph A2, wherein identifying the composition of the identified healthy secretion involves identifying lactic acid.

A4. The method of paragraph A3, wherein identifying lactic acid involves identifying racemic lactic acid having a racemic index in a range of about 50% L/50% D.

A5. The method of paragraph A4, wherein selecting lactic acid involves choosing an approximately racemic mixture with between 30% to 70% L and between 70% to 30% D.

A6. The method of paragraph A5, wherein formulating the topical gel involves formulating the topical gel to include about 1% of the selected lactic acid.

A7. The method of paragraph A2, wherein formulating the topical gel involves bio-balancing the topical gel by avoiding inclusion of one or more ingredients that are toxic to microbiota of the generally healthy vagina.

B. A topical gel for human use, the gel comprising: a formulation matched to a chemistry of a particular part of a human body, the formulation including lactic acid.

B1. The gel of paragraph B, wherein the particular part of the human body is a vagina.

B2. The gel of paragraph B1, wherein the chemistry is a generally healthy chemistry associated with the vagina.

B3. The gel of paragraph B2, wherein the generally healthy chemistry includes lactic acid having a racemic index of about 50% L/50% D.

B4. The gel of paragraph B3, wherein the formulation comprises approximately 1% lactic acid having a racemic index in a range of about 30% L/70% D to 70% L/30% D.

B5. The gel of paragraph B4, wherein the racemic index of the 1% lactic acid is approximately 50% L/50% D.

C. A topical gel for human use, the gel comprising: a formulation matched to a chemistry of a particular part of a human body, the formulation including lactic acid having a racemic index in a range of about 50% L/50% D.

C1. The gel of paragraph C, wherein the particular part is a vagina.

C2. The gel of paragraph C1, wherein the chemistry corresponds to a generally healthy chemistry associated with flora of the vagina.

C3. The gel of paragraph C2, wherein the generally healthy chemistry includes racemic lactic acid having a racemic index of about 50% L/50% D.

C4. The gel of paragraph C3, the lactic acid of the formulation comprises about 1% of the formulation.

D. A vaginal lubricant, comprising: a formulation including lactic acid having a racemic index that is bio-matched but not bio-identical to a racemic index of natural lubricants in a healthy vagina.

D1. The lubricant of paragraph D, wherein the lactic acid of the formulation is naturally-derived.

D2. The lubricant of paragraph D, wherein the lactic acid of the formulation is synthetically-derived.

D3. The lubricant of paragraph D, wherein the racemic index of the lactic acid of the formulation is in a range of about 30% L/70% D to 70% L/30% D, and the racemic index of the natural lubricants is about 50% L/50% D.

D4. The lubricant of paragraph D3, wherein the lactic acid of the formulation is synthetic lactic acid comprising about 1% of the formulation, the synthetic lactic acid having a racemic index of about 50% L/50% D.

D5. The lubricant of paragraph D, wherein vagina bacteria of the healthy vagina is dominated by *Lactobacillus crispatus* which produce lactic acid that is included in the natural lubricants, the lactic acid of the natural lubricants having a racemic index of approximately 50% L/50% D.

D6. The lubricant of paragraph D5, wherein the lactic acid of the formulation has a racemic index in a range of 80% L/20% D to 20% L/80% D, thereby resulting in the formulation being bio-matched to the natural lubricants of the healthy vagina.

The disclosure set forth herein encompasses multiple distinct embodiments with independent utility. These embodiments are not to be considered in a limiting sense as numerous variations are possible. Each example defines an embodiment disclosed in the foregoing disclosure, but any one example does not necessarily encompass all features or combinations that may be eventually claimed. Where the description recites "a" or "a first" element or the equivalent thereof, such description includes one or more such elements, neither requiring nor excluding two or more such elements. Further, ordinal indicators, such as first, second or third, for identified elements are used to distinguish between the elements, and do not indicate a required or limited number of such elements, and do not indicate a particular position or order of such elements unless otherwise specifically stated.

[1] Seyoum Ayehunie, Ying-Ying Wang, Timothy Landry, Stephanie Bogojevic, Richard A Cone, Hyperosmolal vaginal lubricants markedly reduce epithelial barrier properties in a three-dimensional vaginal epithelium model, Toxicology Reports 5 (2018) 134-140.

[2] Rachna Rastogi, Jonathan Su, Alamelu Mahalingam, Justin Clark, Samuel Sung, Thomas Hope, Patrick F. Kiser, Engineering and characterization of simplified vaginal and seminal fluid simulants, Contraception 93 (2016) 337-346.

What is claimed is:

1. A topical substance for vaginal use, the topical substance comprising:
    a solvent;
    a viscosity modifier;
    at least one salt; and
    from 0.2 to 2% by weight of lactic acid which is a mixture of a D-lactic acid and a L-lactic acid,
        wherein the topical substance has an osmolality from 100 mOsm/Kg to 500 mOsm/Kg and a pH from 3.0 to 6.0.

2. The topical substance according to claim 1, wherein the lactic acid has a racemic index from about 30 L/70 D to about 70 L/30 D.

3. The topical substance according to claim 1, wherein the lactic acid has a racemic index of about 50 L/50 D.

4. The topical substance according to claim 1, wherein the topical substance is isotonic with human vaginal fluid.

5. The topical substance according to claim 1, wherein the topical substance is in a form selected from the group consisting of a gel, a cream, a lubricant, an ointment, and a suppository.

6. The topical substance according to claim 1, wherein the pH of the topical substance is from 3.0 to 5.0.

7. The topical substance according to claim 1, wherein the pH of the topical substance is from 3.0 to 4.5.

8. The topical substance according to claim 1, wherein the topical substance comprises:
    from 0.002 to 1.6% by weight of potassium salt; and
    from 0.1 to 1.5% by weight of sodium salt,
    wherein a racemic index of the lactic acid is from about 20 L/80 D to about 80 L/20 D and the topical substance has a pH from 3.0 to 5.0.

9. The topical substance according to claim 8, wherein the topical substance further comprises from 0.005 to 0.12% by weight of calcium salt.

10. A method for manufacturing a topical substance that is isotonic with healthy human vaginal fluids, the method comprising adding into a solvent, a viscosity modifier, a plurality of salts, and one or more acid,
    wherein the one or more acid is lactic acid that is a mixture of a D-lactic acid and a L-lactic acid and added at an amount from 0.2 to 2% by weight of the topical substance,
    the topical substance has a pH from 3.0 to 5.0, and
    an osmolality of the topical substance is from 100 mOsm/Kg to 500 mOsm/Kg.

11. The method of claim 10, wherein the lactic acid has a racemic index of from 30 L/70 D to 70 L/30 D.

12. The method of claim 10, wherein the lactic acid has a racemic index of about 50 L/50 D.

13. The method of claim 10, wherein the pH of the topical substance is from 3.0 to 4.5.

14. The method of claim 10, wherein the plurality of salts comprises:
   from 0.002 to 1.6% by weight of potassium salt;
   from 0.1 to 1.5% by weight of sodium salt; and
   wherein a racemic index of the lactic acid is from about 20 L/80 D to about 80 L/20 D and the topical substance has a pH from 3.0 to 5.0.

15. The method of claim 14, wherein the plurality of salts further comprises from 0.005 to 0.12% by weight of calcium salt.

16. A method for improving lubrication of a vagina of a subject in need thereof, comprising applying an effective amount of the topical substance in the form of the lubricant according to claim 5 to the vagina of the subject, wherein the applied amount is effective so as to increase the lubrication in the vagina of the subject compared with that of a subject that has not been administered the topical substance.

17. A method for improving vaginal moisture of a subject in need thereof, comprising applying an effective amount of the topical substance according to claim 1 to the vagina of the subject, wherein the applied amount is effective so as to increase the moisture in the vagina of the subject compared with that of a subject that has not been administered the topical substance.

18. The method according to claim 16, wherein a pH of a vaginal fluid of the subject after applying the topical substance is from 3.0 to 6.0, and the osmolality of the fluid is 100 mOsm/Kg to 500 mOsm/Kg.

19. The method according to claim 17, wherein a pH of a vaginal fluid of the subject after applying the topical substance is from 3.0 to 6.0, and the osmolality of the fluid is 100 mOsm/Kg to 500 mOsm/Kg.

20. A method for improving a vaginal biome of a subject in need thereof, comprising applying an effective amount of the topical substance according to claim 1,
   wherein the applied amount is effective so as to increase a proportion of D-lactic acid within a total lactic acid produced by the vaginal biome or reduce a pH of a vaginal fluid of the subject as compared with a vagina of a subject that has not been administered the topical substance.

21. A method for maintaining a healthy vaginal biome of a subject, comprising applying an effective amount of the topical substance according to claim 1 to the vagina of the subject,
   wherein the vaginal biome of the subject produces lactic acid having a proportion of D-lactic acid higher than 20%, and a pH of a vaginal fluid of the subject is from 3.0 to 4.5.

22. A method for reducing a risk of developing at least one condition selected from the group consisting of bacterial vaginosis, vaginal dysbiosis, and an unhealthy vaginal condition; or reducing a susceptibility to sexually transmitted infection of a subject, comprising applying an effective amount of a topical substance with components of healthy human vaginal fluids to a vagina of a subject in need thereof,
   wherein a vaginal biome of the subject after applying the topical substance produces lactic acid having a higher proportion of D-lactic acid compared with a subject that has not been administered the topical substance; or a vaginal fluid of the subject has a lower pH compared with the subject that has not been administered the topical substance; and
   the subject administered the topical substance has a lower risk of developing at least one condition selected from the group consisting of bacterial vaginosis, vaginal dysbiosis, and an unhealthy vaginal condition; or a reduced susceptibility to sexually transmitted infection compared with a subject that has not been administered the topical substance,
   wherein in the unhealthy vaginal condition, the vaginal biome of the subject produces lactic acid having a proportion of D-lactic acid lower than 20% of a total lactic acid or the pH of the vaginal fluid of the subject is higher than 4.5.

* * * * *